United States Patent [19]

Ducheyne et al.

[11] Patent Number: 5,373,621
[45] Date of Patent: Dec. 20, 1994

[54] POROUS COATED IMPLANTS HAVING IMPROVED FATIGUE BEHAVIOR

[75] Inventors: Paul Ducheyne, Rosemont, Pa.; Debra Wolfarth, Mt. Laurel, N.J.

[73] Assignee: The Trustees of the University of Pennsylvania, Philadelphia, Pa.

[21] Appl. No.: 97,420

[22] Filed: Jul. 26, 1993

Related U.S. Application Data

[62] Division of Ser. No. 726,829, Jul. 8, 1991, Pat. No. 5,258,030.

[51] Int. Cl.⁵ .............................................. B23P 17/00
[52] U.S. Cl. .................................. 29/527.2; 427/422; 428/613; 623/16; 623/23
[58] Field of Search ............... 427/422; 29/527.2; 623/16, 23; 428/613

[56] References Cited

U.S. PATENT DOCUMENTS

| | | |
|---|---|---|
| 448,745 | 3/1891 | Wright . |
| 3,314,420 | 4/1967 | Smith et al. . |
| 3,605,123 | 9/1971 | Hahn . |
| 4,923,513 | 5/1990 | Ducheyne et al. . |
| 5,030,233 | 7/1991 | Ducheyne . |
| 5,258,030 | 11/1993 | Wolfarth et al. . |

FOREIGN PATENT DOCUMENTS

| | | |
|---|---|---|
| 1122634 | 9/1956 | France . |
| 90-1376 | 2/1990 | WIPO .................................. 427/422 |

OTHER PUBLICATIONS

J. Biomed Mater Res. (USA), 1990, 24/5 pp. 591–604 by P. B. Messersmith et al.

D. Wolfarth, et al., "The effect of stress concentrations on fatigue properties of porous coated implants," Trans. 13th Ann. Northeast Bioengineering Conference, Philadelphia, Pa. (Mar. 1987) (Abstract only).

P. B. Messersmith, et al., "Stress enhancement and fatigue susceptibility of porous coated Ti–6Al–4V implants: an elastic analysis," J. Biomed. Mater. Res., 24:591–604 (1990).

D. Wolfarth, et al., "Parametric analysis of interfacial stress concentrations in porous coated implants," J. Applied Biomater., 1:3–12 (1990).

S. D. Cook, et al., "Fatigue properties of carbon–and porous–coated Ti–6Al–4V alloy," J. Biomed. Mater. Res., 18:497–512 (1984).

S. D. Cook, et al., "The effect of post-sintering heat treatments on the fatigue properties of porous coated Ti–6Al–4V Alloy," J. Biomed. Mater. Res., 22:287–302 (1988).

K. W. Greer, et al., "Fatigue properties of porous coated Ti–6Al–4V devices," pp. 228–231 in Proc. Fourth Southern Biomed. Eng. Conf., Pergamon Press, New York, 1985.

D. H. Kohn, et al., "A parametric study of the factors affecting the fatigue strength of porous coated Ti–6Al–4V implant alloy," J. Biomed. Mater. Res., 24:1483–1501 (1990).

S. Yue, et al., "The fatigue strength of porous–coated Ti–6Al–4V implant alloy," J. Biomed. Mater. Res., 18:1043–1058 (1984).

Primary Examiner—Carl J. Arbes
Attorney, Agent, or Firm—Woodcock Washburn Kurtz Mackiewicz & Norris

[57] ABSTRACT

Orthopaedic implants exhibiting improved fatigue strength are disclosed. By forming a plurality of nodules on the surface of an implant and depositing a porous coating onto the surface of these nodules, the fatigue strength of implants such as those made from $\alpha+\beta$ titanium alloys, e.g., Ti–6Al–4V alloy is substantially improved. The present invention provides a novel geometry which substantially reduces the stress concentration factor created by the interfacial geometry of conventional porous coatings. Methods of manufacturing porous coated orthopaedic implants are also disclosed.

10 Claims, 2 Drawing Sheets

POROUS COATED IMPLANTS HAVING IMPROVED FATIGUE BEHAVIOR

This is a division of application Ser. No. 07/726,829, filed Jul. 8,1991, issued as U.S. Pat. No. 5,258,030 on Nov. 2, 1993.

The present invention relates to orthopaedic implants. More particularly, the present invention relates to methods for improving the fatigue behavior of porous coated implantable structures such as hip replacements.

BACKGROUND OF THE INVENTION

Fixation of a total hip replacement or other implant to the skeletal system is one of the most important problems in the field of orthopaedic biomaterials. Porous coated implants offer the potential for superior fixation and are being studied for use in a young, active patient population. However, porous coated implants are subjected to fatigue under the repetitive load of walking. It is known that porous coated metals have a reduced fatigue strength compared to the uncoated material. For example, porous coated Ti-6Al-4V, a typical $\alpha+\beta$ titanium implant alloy, has a fatigue strength that is approximately one-third that of the uncoated material.

The reduction in fatigue strength has been attributed to two important factors. One factor is the microstructure that results from sintering the coating to the implant above the $\beta$ transus temperature. Experiments have been conducted to address this reason for the fatigue strength reduction of Ti-6Al-4V. As a result, the microstructure of porous coated Ti-6Al-4V has been modified utilizing post-sintering heat treatments that refine the lamellar structure most often found after the sintering procedure. A new, fine-grained structure which leads to a fatigue strength that is superior to that of the presintered, equiaxed structure has been developed as a result. See U.S. Pat. No. 4,923,513—Ducheyne et al., which is incorporated herein by reference. However, although smooth specimen fatigue strength can be improved with changes in microstructure, porous coated specimen strength cannot. It has been found that porous coated Ti-6Al-4V has the same fatigue strength regardless of microstructure.

The second factor affecting fatigue strength is the interfacial geometry between the porous coating and the substrate, which creates stress concentrations. The effect of microstructure on fatigue strength reduction of porous coated Ti-6Al-4V is in fact outweighed by the effect of interfacial geometry with current porous coatings. Investigators have created numerical models of the interfacial geometry between the porous coating and substrate. See D. Wolfarth, et al., "The effect of stress concentrations on fatigue properties of porous coated implants," *Trans. 13th Ann. Northeast Bioengineering Conference*, Philadelphia, Pa. (March, 1987); P. B. Messersmith, et al., "Stress enhancement and fatigue susceptibility of porous coated Ti-6Al-4V implants: an elastic analysis," *J. Biomed. Mater. Res.*, 24:591–604 (1990); D. Wolfarth, et al., "Parametric analysis of interfacial stress concentrations in porous coated implants," *J. Applied Biomater.*, 1:3–12 (1990). These investigators have found that varying the interfacial radius affects the value of stress concentrations, quantified by the stress concentration factor, $K_t$. It has also been found that varying the contact area between a coating particle and the substrate affects the value of $K_t$. The measured values of interfacial radius and contact area on a porous coated hip stem has led to the discovery of a range of values for each which corresponded to a range in values of $K_t$ from 2 to 5.5. From these data it was concluded that by virtue of the current wide range in $K_t$ values, sintering process improvements to consistently produce a low value of $K_t$ around all sintered particles and hence an improved interfacial geometry for conventional coatings would not be reasonably possible. Thus, while it has been shown that an increase in sintering time and/or temperature may reduce the magnitude of the resulting stress concentrations, the interfacial radius, one important parameter that can be varied to reduce stress concentrations, is not significantly affected by specifics of the sintering process.

Therefore, there remains a need to improve the reduced fatigue strength of porous coated Ti-6Al-4V and other $\alpha+\beta$ titanium alloys, as well as other alloys used in implants. The current structures present a serious impediment to the design of porous coated implants. For example, current porous coatings are often not applied to the lateral surface of hip stems because stresses are highest there. However, bone ingrowth occurs preferentially on the lateral surface. Furthermore, to make up for the reduced strength of the coated material, much larger prostheses are used. These prostheses have an increased cross-sectional moment of inertia and thereby minimize stress transfer to the surrounding bone. The net biological effect is that these prostheses lead to adverse bone tissue remodeling which can eventually lead to loosening of the device.

As explained above, current coatings cannot provide an interfacial geometry that leads to a consistent reduction in stress concentrations. Therefore, it would be desirable to determine the factors that create stress concentration factors in porous coated implants in order to provide a rational basis for analysis. Accordingly, it is an object of the present invention to minimize the stress concentration factor, $K_t$, by selecting an optimal implant/coating geometry.

SUMMARY OF THE INVENTION

The present invention thus provides an orthopaedic implant for promoting bone ingrowth comprising an implant substrate having one or more nodules formed thereon; a porous coating is affixed to at least a portion of the nodules. In a preferred embodiment, the nodules are a set of parallel ridges forming rectangular shaped raised areas. In yet another preferred embodiment, the nodules result from two intersecting sets of parallel troughs to form rectangular or lozenge shaped elevated areas. Most preferably, the height of the nodules is greater than about 1 mm (0.040 inches) above the surface of the substrate for a nodule radius to nodule width ratio of 0.4. In a most preferred embodiment, the orthopaedic implant of the present invention is comprised of Ti-6Al-4V alloy and the porous coating is comprised of a plurality of powders, e.g. substantially spherical or non-spherical particles, a plasma sprayed porous coating, or randomly oriented wire meshes or orderly oriented wire meshes, or fibers.

The present invention also discloses methods of manufacturing a porous coated orthopaedic implant comprising the steps of forming the substrate having one or more nodules on the surface of a section thereof, and applying a porous coating to the surface of the nodules. Preferably, the step of applying a porous coating comprises sintering a plurality of powders, wires or fibers to the nodule surface. Alternatively, a porous coating can be applied first, subsequent to which the nodule pattern is machined into the substrate.

DETAILED DESCRIPTION OF THE PREFERRED EMBODIMENTS

The present invention provides an unconventional geometry that leads to reduced stress concentrations and to more than twice the fatigue strength of current porous coated specimens. This invention, the porous coated nodule, can be machined consistently with values of interfacial radius and contact area that lead to a low value of the stress concentration factor, $K_t$. It has now been found that the addition of the porous coating to the surface of the nodule does not lead to an increase in $K_t$ if the nodule height is greater than a critical height. By creating numerical models and subsequently verifying the models with fatigue testing it has been shown that a reduction in stress concentration, $K_t$, and an improvement in the fatigue strength of the material for porous coated implants is achieved with the present invention.

Figure 1:
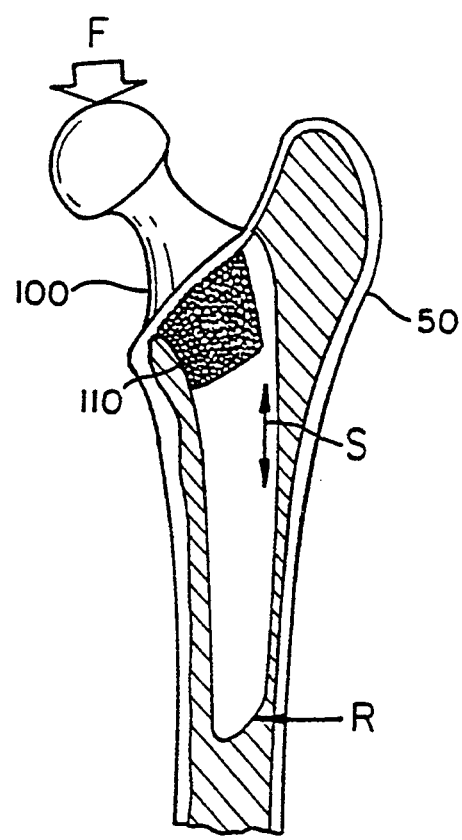
FIG. 1 is side elevation view of a typical implant in the upper femur.

A typical porous coated implant is illustrated in FIG. 1. As shown, the implant 100 illustrated is part of a total hip replacement and is inserted into the upper femur 50 of a patient. The arrow marked F illustrates the general direction of the forces created by the normal loading placed upon the implant 100, while the arrow marked R illustrates the general direction of the reaction force. As shown by the arrow marked S, since these two forces create a bending moment at least a portion of the lateral surface of the implant 100 is placed in tension. Since the loading condition varies as the patient moves about, repetitive loading and unloading of the implant creates fatigue loading. Also visible in FIG. 1 is the porous coated portion 110 of the implant 100. As known to those of ordinary skill, such porous coated portions are necessary to promote bone ingrowth and achieve permanent fixation.

Figure 2:
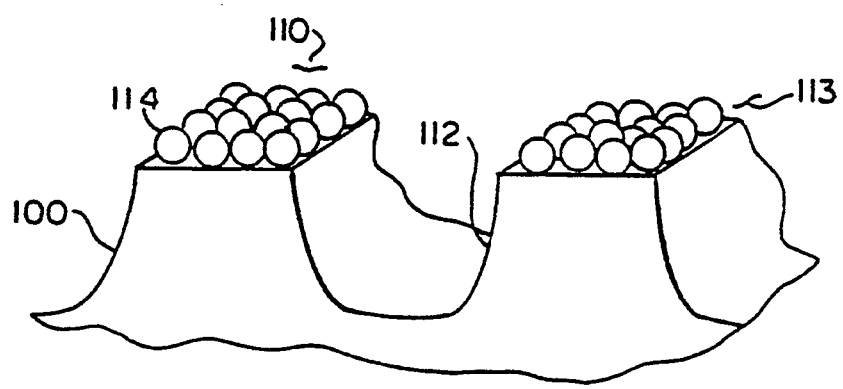
FIG. 2 illustrates an enlarged portion of the implant of FIG. 1 made in accordance with the present invention.

As explained above, conventional porous coated surfaces suffer from poor fatigue resistance. It has now been found, however, that the fatigue resistance can be markedly improved by creating one or more nodules on the surface of the implant and applying a porous coating only to the top surface of the nodules. Referring now to FIG. 2, there is shown a greatly enlarged perspective view of a portion of the porous coated section 110 of an implant 100 made in accordance with the present invention. The nodules 112 are essentially flat topped ridges that extend above the surface of the implant 110. In terms of the present invention, a "nodule" is any structure that rises above the nominal surface of the implant. For example, the ridges illustrated in FIG. 2 can be formed by machining "troughs" into the surface of an implant. If an intersecting course of troughs are also cut, a "checkered" pattern of lozenge-shaped nodules will result. As will be understood by those of ordinary skill, the patterns of the nodules are limited only by the machining and surface forming techniques that are available. For different types of implants, different geometries will be found to be optimal. The porous coating 114, illustrated as beads of material, is applied only to the top surface 113 of the nodules 112. Thus, in terms of the present invention, the surface of the implant is defined as all outer material of a device as currently designed, and can include the material in recesses on for example, the implant stem as well.

Figure 3:
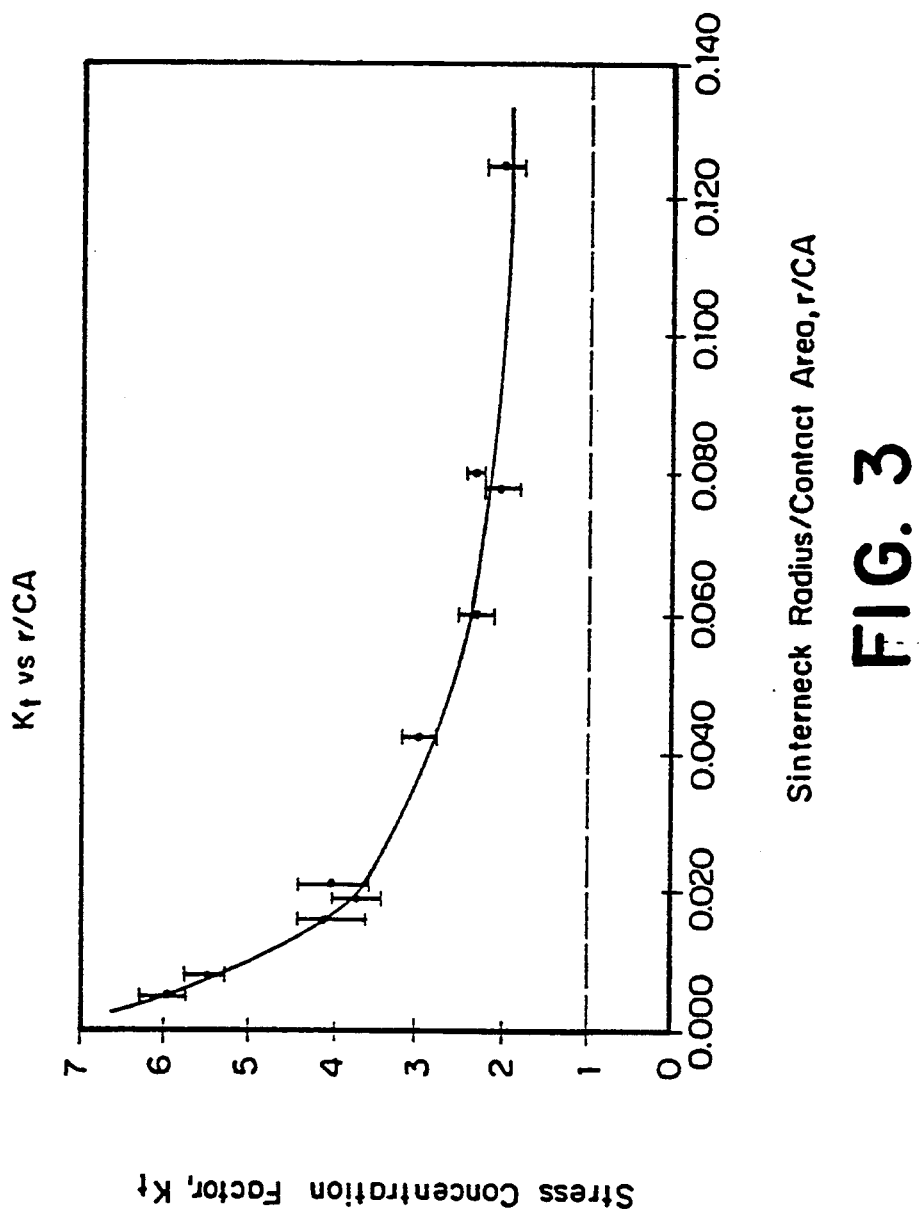
FIG. 3 is a plot showing the theoretical relationship between stress concentration, and the ratio of sinterneck radius and contact area for beaded porous coatings in tension or bending.

The fatigue resistance improvement provided by nodules of the present invention has been derived mathematically using finite element analysis and verified through experimental testing. Mathematical analysis of conventional beaded porous coatings showed that the magnitude of the stress concentration factor, $K_t$, was dependent upon the ratio r/CA, where r represents the sinterneck radius between a bead and the substrate and CA represents the contact area between the bead and the substrate. As illustrated in FIG. 3, the shape of the $K_t$ v. r/CA curve in tension or bending is governed by two asymptotes. As the sinterneck radius is reduced, r/CA approaches zero and the interfacial geometry approaches a sharp crack, the stresses become infinitely large and the stress concentration factor approaches infinity. Alternatively, as the sinterneck radius gets infinitely large and the contact area approaches zero, the interfacial geometry approaches a smooth substrate. Thus, as r/CA approaches infinity, the maximum stress approaches the nominal stress and the stress concentration factor approaches unity. The details of these analyses and the finite element model of the interfacial geometry are disclosed in Wolfarth, D., "*The Effect of Interfacial Geometry on the Fatigue Strength of Ti-6Al-4V Implant Alloy*, Ph.D. Thesis, University of Pennsylvania, 1991, which is incorporated by reference as if fully set forth herein.

Based upon these analytical results disclosed in the above-referenced Wolfarth thesis, it was determined that the nodule geometry described above with reference to FIG. 2 would provide an improved geometry for the surface of an implant since they could be formed with a very large radius and a relatively small contact area. However, the geometry of the nodules does not provide a matrix for bone ingrowth; only ongrowth is possible without interdigitation within or between nodules. Bone ingrowth can transfer tensile stresses between the implant and bone which is thought to lead to more physiologic stress transfer to the bone. Beads sintered to the surface of nodules as shown in FIG. 2, or also a wire mesh or fibers sintered to it can provide the necessary interdigitation for bone ingrowth.

The requirements to reduce $K_t$ under tension and shear loading are not the same. Shear and tension loading must both be considered important when addressing failure of a porous coated system. Contact area needs to be increased in order to reduce stress under a shear load. However, nodule width which is the contact area of the nodule needs to be decreased in order to reduce stress under a tensile load. The nodules of the present invention have the advantage that parameters can be optimized under both tensile and shear loads. Thus, instead of having to compromise the value for contact area in terms of both loading conditions, the best contact area can be used at the top of the nodule satisfying shear load condition. With reference to FIG. 2, the nodules have a base width which is relatively small to avoid significant stress flow into the nodule under tension. The contact area between the particles and the top surface of the nodule is relatively large compared to the sinterneck radius, which is of benefit under shear.

Theoretically, the porous coating will not cause a high stress concentration if placed on top of the nodules. The analysis described above has led to the observation that stresses within single porous coating particles are much lower than stresses in the substrate. Since a single nodule is analogous to a single porous coating particle, the stresses in the nodule should be lower than the stresses in the substrate. Thus, beads sintered to the nodule surface should lead to lower stresses than beads sintered to a flat substrate. It should be noted that although sintered wire, fiber or powder coatings can be useful with the present invention, a preferred embodiment is porous coatings which do not bridge the gap between nodules, since connecting the nodules prevents the nodules from moving apart under tensile loading conditions, thereby reducing the benefits of the geometry described above.

More potential for bone ingrowth exists using particle-coated nodules having a large porous coated area. Wide individual nodules lead to the largest area for ingrowth. However, wide nodules have a large contact area, which leads to a large stress concentration factor. Moreover, as pointed out above, the height of the nodule should be minimized. It is advantageous to minimize the height of the nodule for several reasons. With a constant nodule root radius, the top surface of the nodule is larger. There is also a minimization of the troughs between the nodules in certain embodiments. Finally, the outer dimension of the prosthesis including the nodules can be limited. With decreasing height, the benefit of having the surface nodule is lost as the nodule begins to approach a flat substrate. It is therefore important to determine the lowest height of a nodule that does not lead to an increase in the stress concentration factor, $K_t$. The critical height is thus defined as the lowest height that does not lead to a value of $K_t$ at the coating/nodule interface greater than $K_t$, at the nodule radius.

Experimental data was collected using a notch as the stress concentrator to validate the calculations that determined the height at which stress increases occur. A notch was chosen instead of the interfacial porous coating geometry in order to facilitate specimen manufacture. A notch simulates the notch-like radius of a porous coating particle and notched specimens can reproducibly be made
more quickly and at less expense than porous coated specimens. Two specimen geometries were designed based on numerical models, and were tested in accordance with ASTM standard E466 for high cycle fatigue specimens using a rotating beam bending machine. The details of these tests, the results and comparisons to date reported in the literature is found in D. Wolfarth, *The Effect of Interfacial Geometry on the Fatigue Strength of Ti-6Al-4V Implant Alloy*, Ph.D. Thesis, University of Pennsylvania (1991), which is incorporated by reference as if fully set forth herein. The nodules in the model calculations had an r/CA value of 0.4 leading to a $K_t$ value equal to 1.4. Three nodule heights were chosen for the numerical study: 1.11 mm (0.044 inches), 0.96 mm (0.038 inches), and 0.56 mm (0.022 inches). At the largest height, no increase in stress was calculated. At the middle height, the stress was the same at the notch tip and at the nodule radius. At the smallest height, the stress increased to a value above that at the nodule radius. Thus, with a nodule height of about 1 mm, with an r/CA value of 0.4, $K_t$ was found to have a value of about 1.4 ($\pm 0.1$). This represents a significant reduction in the stress concentration factor from conventional porous substrates where the value of $K_t$ was found to be between about 2.0–5.5. The experiments showed that at the larger nodule height, i.e., 1.00 mm, the fatigue strength was 305 MPa, at the smaller height, i.e., 0.5 mm, the fatigue strength was 132 MPa. A height of about 1.00 mm (0.040 inches) is thus optimum for this particular nodule geometry illustrated and described above, characterized by its root radius, 2.5 mm (0.1 inches), and its base width, 6.25 mm (0.25 inches). Other nodule geometries will have different optimum height values.

Prior investigators have reported fatigue strengths for porous coated Ti-6Al-4V specimens ranging between 140 and 217 MPa. See S. D. Cook, et al., "Fatigue properties of carbon- and porous-coated Ti-6Al-4V alloy," *J. Biomed. Mater. Res.*, 18:497–512 (1984); S. D. Cook, et al., "The effect of post-sintering heat treatments on the fatigue properties of porous coated Ti-6Al-4V alloy," *J. Biomed. Mater. Res.*, 22:287–302 (1988); K. W. Greer, et al., "Fatigue properties of porous coated Ti-6Al-4V devices," p 228–231 in *Proc. Fourth Southern Biomed. Eng. Conf.*, Pergamon Press, New York, 1985; D. H. Kohn et al., "A parametric study of the factors affecting the fatigue strength of porous coated Ti-6Al-4V implant alloy," *J. Biomed. Mater. Res.*, 24:1483–1501 (1990); S. Yue, et al., "The fatigue strength of porous-coated Ti-6Al-4V implant alloy," *J. Biomed. Mater. Res.*, 18:1043–1058 (1984). However, none of these reported values were calculated taking into account the effects of the coating thickness. Thus, the true fatigue strengths are somewhat lower than those reported, and if recalculated would be between about 117–163 MPa. The fatigue strength of implant materials made in accordance with the present invention, 305±12 MPa, is significantly higher than these reported values.

The present invention therefore provides a unique geometry that improves the fatigue strength of porous coated implants using current porous coatings. The interfacial geometry disclosed herein is based upon mathematical models verified by experimental testing and comparison to conventional porous coated materials. Additionally, the nodules disclosed herein can be accurately and repeatedly formed on the surface of the substrate using conventional technology.

Although certain embodiments of the present invention have been discussed in detail above, the present invention is by no means limited to these illustrative embodiments. For example, other alloys and/or biomaterials used for implants will benefit from the nodule geometry disclosed herein. Moreover, although the present invention has been verified with reference to the stresses created in a hip implant, the concepts disclosed herein are generally applicable to any implant that undergoes cyclic stress. Upon review of this specification, those of ordinary skill in the art will immediately realize that there are numerous useful modifications, adaptations and applications of the invention disclosed. Accordingly, in order to ascertain the scope of the present invention, reference should be made to the appended claims.

What is claimed is:

1. A method of manufacturing a porous coated orthopaedic implant comprising the steps of:

forming at least one ridge between two troughs to define a nodule extending upwardly from a substrate, the troughs having a bottom surface and the nodule having a distal surface; and applying a porous coating to the implant so that only to the distal surface of the nodule has the porous coating.

2. The method of claim 1, wherein the step of applying a porous coating comprises sintering a plurality of substantially spherical beads to at least the distal surface of the nodule.

3. The method of claim 1, wherein the step of applying a porous coating comprises depositing a plurality of particles on at least the distal surface of the nodule.

4. The method of claim 1, wherein the step of applying a porous coating comprises depositing a plurality of wires on the distal surface of at least two nodules that extend discontinuously between nodules.

5. The method of claim 1, wherein the step of applying a porous coating comprises depositing a plurality of fibers on the distal surface of at least two nodules that extend discontinuously between nodules.

6. The method of claim 1, wherein the step of applying a porous coating comprises applying a coating to the implant and removing coating that is adhered to the implant in areas other that the distal surface of the nodule.

7. The method of claim 1, wherein the step of applying a porous coating comprises: masking the implant to leave only the distal surface of one or more nodules exposed; and applying a coating to the implant.

8. A method of manufacturing a porous coated orthopaedic implant, comprising the steps of:

applying a porous coating to a surface of the implant; and forming one or more nodules on the surface of the implant by cutting through the coating.

9. The method of claim 8 wherein the nodules are formed by cutting a plurality of troughs in the coating.

10. The method of claim 9 wherein two or more of the troughs intersect.

* * * * *